United States Patent
Shih et al.

(10) Patent No.: US 8,189,183 B2
(45) Date of Patent: May 29, 2012

(54) OPTICAL INSPECTION APPARATUS

(75) Inventors: Hsueh-Ching Shih, Taipei County (TW); Jia-Huey Tsao, Taipei County (TW); Chih-Cheng Feng, Taipei County (TW); Chun-Lin Chiang, Taipei County (TW); Chun-Min Su, Taichung County (TW); Kuo-Chi Chiu, Hsinchu County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 295 days.

(21) Appl. No.: 12/580,619

(22) Filed: Oct. 16, 2009

(65) Prior Publication Data

US 2010/0253947 A1      Oct. 7, 2010

(30) Foreign Application Priority Data

Apr. 3, 2009   (TW) ................................ 98111176 A

(51) Int. Cl.
*G01N 21/01* (2006.01)
*G01N 21/55* (2006.01)
*G01M 19/00* (2006.01)

(52) U.S. Cl. ..................... 356/237.1; 356/445; 73/866.5; 73/865.8

(58) Field of Classification Search .................. 73/865.8, 73/865.5, 866.5; 250/201.3, 492.2, 442.11; 356/445, 237.1–237.2; 382/152, 128–133
See application file for complete search history.

(56) References Cited

U.S. PATENT DOCUMENTS

| | | | |
|---|---|---|---|
| 4,600,357 A * | 7/1986 | Coules | 414/730 |
| 5,341,215 A | 8/1994 | Seher | |
| 5,852,298 A * | 12/1998 | Hatakeyama et al. | 250/492.2 |
| 6,987,561 B2 * | 1/2006 | Reznichenko et al. | 356/237.2 |
| 7,262,866 B2 | 8/2007 | Ivarsson | |
| 7,265,844 B2 | 9/2007 | Codner et al. | |
| 7,619,190 B2 * | 11/2009 | Kuo et al. | 250/201.3 |
| 7,719,672 B2 * | 5/2010 | Kohayase et al. | 356/237.2 |
| 7,986,402 B2 * | 7/2011 | Wang et al. | 356/237.1 |
| 2005/0025353 A1 * | 2/2005 | Kaneko et al. | 382/152 |
| 2008/0092672 A1 * | 4/2008 | Gibson et al. | 73/865.8 |
| 2008/0098834 A1 * | 5/2008 | Sergoyan et al. | 73/866.5 |

* cited by examiner

*Primary Examiner* — Sang Nguyen
(74) *Attorney, Agent, or Firm* — WPAT., P.C.; Justin King

(57) ABSTRACT

An optical inspection apparatus capable of adjusting an incident angle of a detected light beam and adjusting a detecting angle for detecting the detected light beam. A driving mechanism is used to actuate two arms having a light source and a detector disposed thereon respectively to conduct a relative movement between the two arms so as to control the incident angle and the detecting angle. By means of the embodiments, mechanism for adjusting the angle is simplified so that the apparatus is capable of being adapted to combine with the application of micro sensors such that practicality of modularization design and microminiaturization and convenience of operation are capable of being greatly improved and that the cost can be reduced.

12 Claims, 11 Drawing Sheets

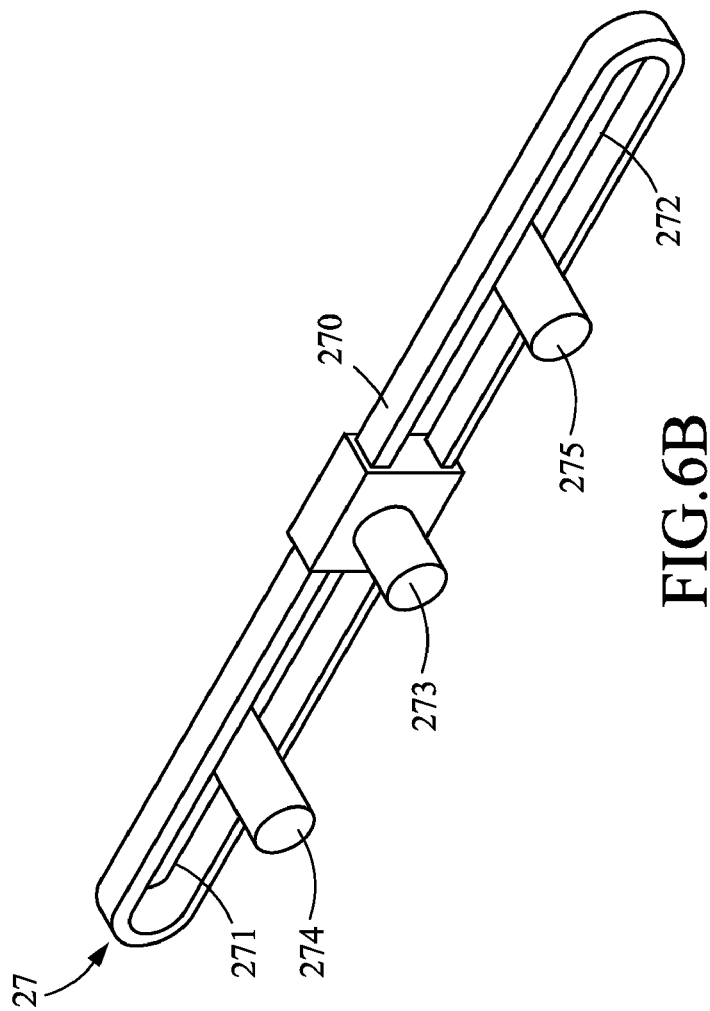
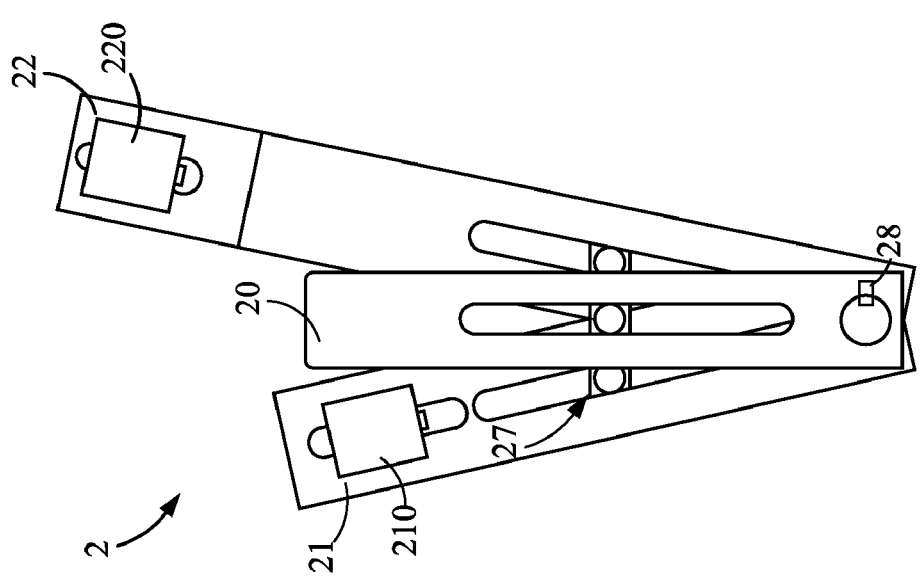
FIG.6B
FIG.6A

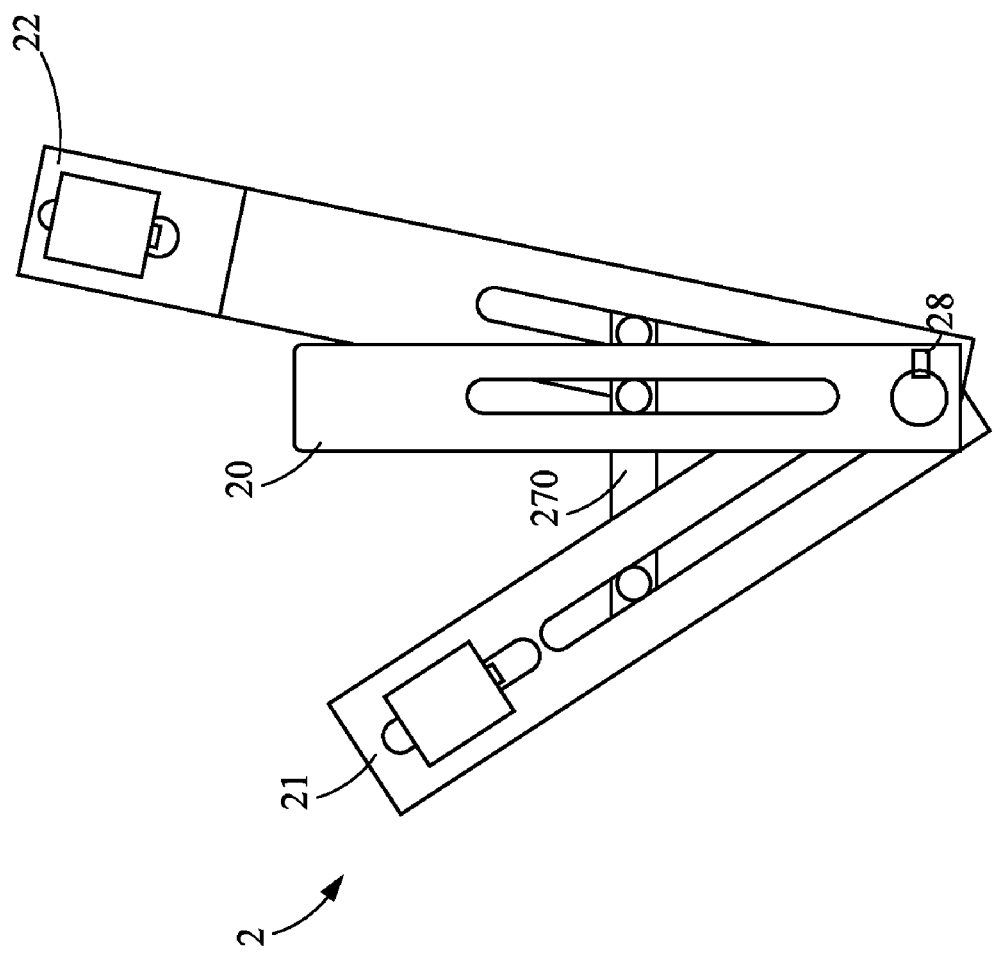

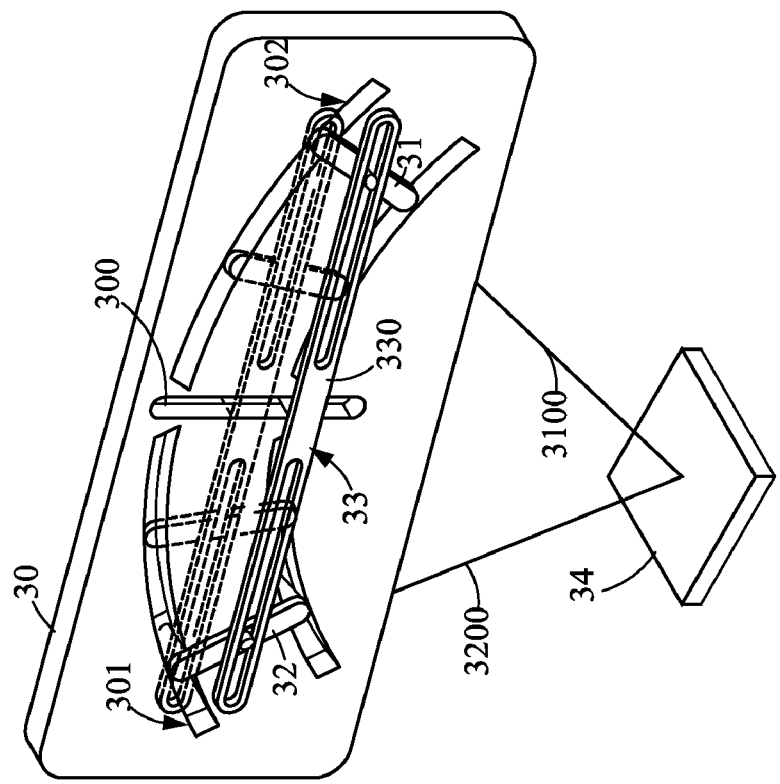
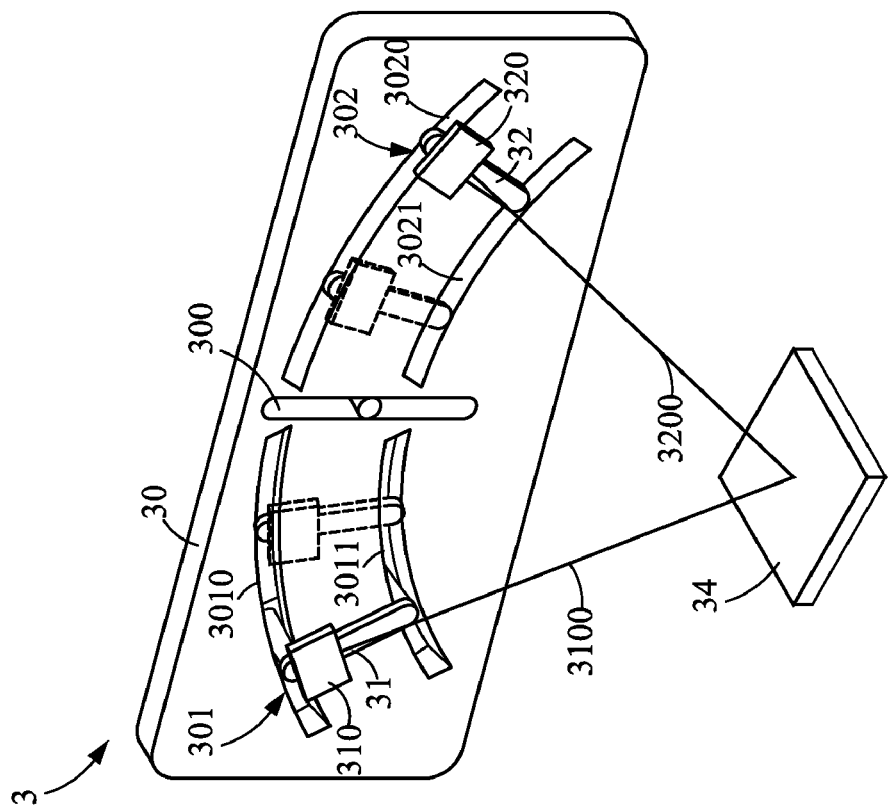
FIG.7A
FIG.7B

OPTICAL INSPECTION APPARATUS

1. TECHNICAL FIELD

The disclosure generally relates to an optical inspection technique and, more particularly, to an optical inspection apparatus capable of adjusting optical angles.

2. TECHNICAL BACKGROUND

For surface plasmon resonance (SPR) measurement, using a grating-type or a prism-type SPR inspection system, the measurement for the SPR angle is a key step. If the angle can be correctly adjusted and the detected signal can be analyzed, high-precision measurement can be achieved. To inspect multiple objects under test by adaptively adjusting the grating pitch, detecting resonance angle variation due to the thickness of the gold film and functional groups, it is required that the system has to be capable of adjusting the SPR angle corresponding to different objects under test.

Conventionally, a major company of SPR instrument, Biacore, discloses in U.S. Pat. No. 7,262,866 that an angle rotating mechanism is used to adjust the angles of the optical reflectors SM1 and SM2 so that the incident light beam reaches the surface of the prism or the grating to inspect SPR.

Moreover, in U.S. Pat. No. 5,341,215, a method and apparatus for detecting the presence and/or concentration of biomolecules by providing a boundary surface between an optically denser medium and an optically rarer medium. The angle of incidence is controlled by rotating a desk such that the intensity of the reflected light is always maintained at a minimum which ensures that the angle of incidence is equal to the angle at which SPR occurs.

Moreover, U.S. Pat. No. 7,265,844 discloses a mechanical linkage (10, 11) of planar mirrors 12 and 13 provides a single point adjustment of angle of incidence and angle of refraction while maintaining a constant optical axis of the light source and detector, as shown in FIG. 1A and FIG. 1B, to achieve optical inspection when an incident angle is equal to the reflected angle.

SUMMARY

In view of the above, the disclosure provides an optical inspection apparatus, comprising: a central shaft device comprising a pivot portion; a first arm with one end pivotally connected to the pivot portion, the first arm being provided with a light source thereon; a second arm with one end pivotally connected to the pivot portion, the second arm being provided with a detector thereon; and a linkage driver portion coupled to the central shaft device, the first arm and the second arm, the linkage driver portion being capable of conducting a movement to drive the first arm and the second arm to move relatively.

The disclosure further provides an optical inspection apparatus, comprising: a first arm being slidingly connected to a first sliding groove portion with a curvature, the first arm further comprising a light source disposed thereon; a second arm being slidingly connected to a second sliding groove portion with a curvature, the second arm further comprising a detector disposed thereon; and a driver portion being coupled to the first arm and the second arm, the driver portion using a driving force applied on the first arm and the second arm to drive the first arm and the second arm to move respectively on the first sliding groove portion and the second sliding groove portion.

BRIEF DESCRIPTION OF THE DRAWINGS

The embodiments of the disclosure will be readily understood by the accompanying drawings and detailed descriptions, wherein:

FIG. 6A is a schematic diagram of an optical inspection apparatus according to a second embodiment of the disclosure;

FIG. 6B is a 3-D schematic diagram of the linkage in FIG. 6A;

FIG. 6C is a schematic diagram showing that the first arm and the second arm move with non-equal angles according to a second embodiment of the disclosure;

FIG. 7A and FIG. 7B are schematic diagrams of an optical inspection apparatus according to a third embodiment of the disclosure.

DETAILED DESCRIPTION OF EMBODIMENTS

The disclosure can be exemplified by but not limited to various embodiments as described hereinafter.

One embodiment of the disclosure discloses an optical inspection apparatus a using linear movement device and linkage mechanism to achieve large angle modulation of polarized reflected light, high-precision small angle tuning and measurement of reflected angle detection so as to optical inspection optimization, and overcome the problems of cost reduction and microminiaturization of angle adjusting mechanism.

Another embodiment of the disclosure discloses an optical inspection apparatus using a guiding groove with a curvature linear movement device and a driver device capable of driving optical emitting devices and receiving devices to move on the guiding groove to change the angles of incident light and reflected light. With such an optical inspection apparatus, reflected light with different angles are detected and the apparatus size can be smaller by simplifying the configuration thereof.

Figure 1A:
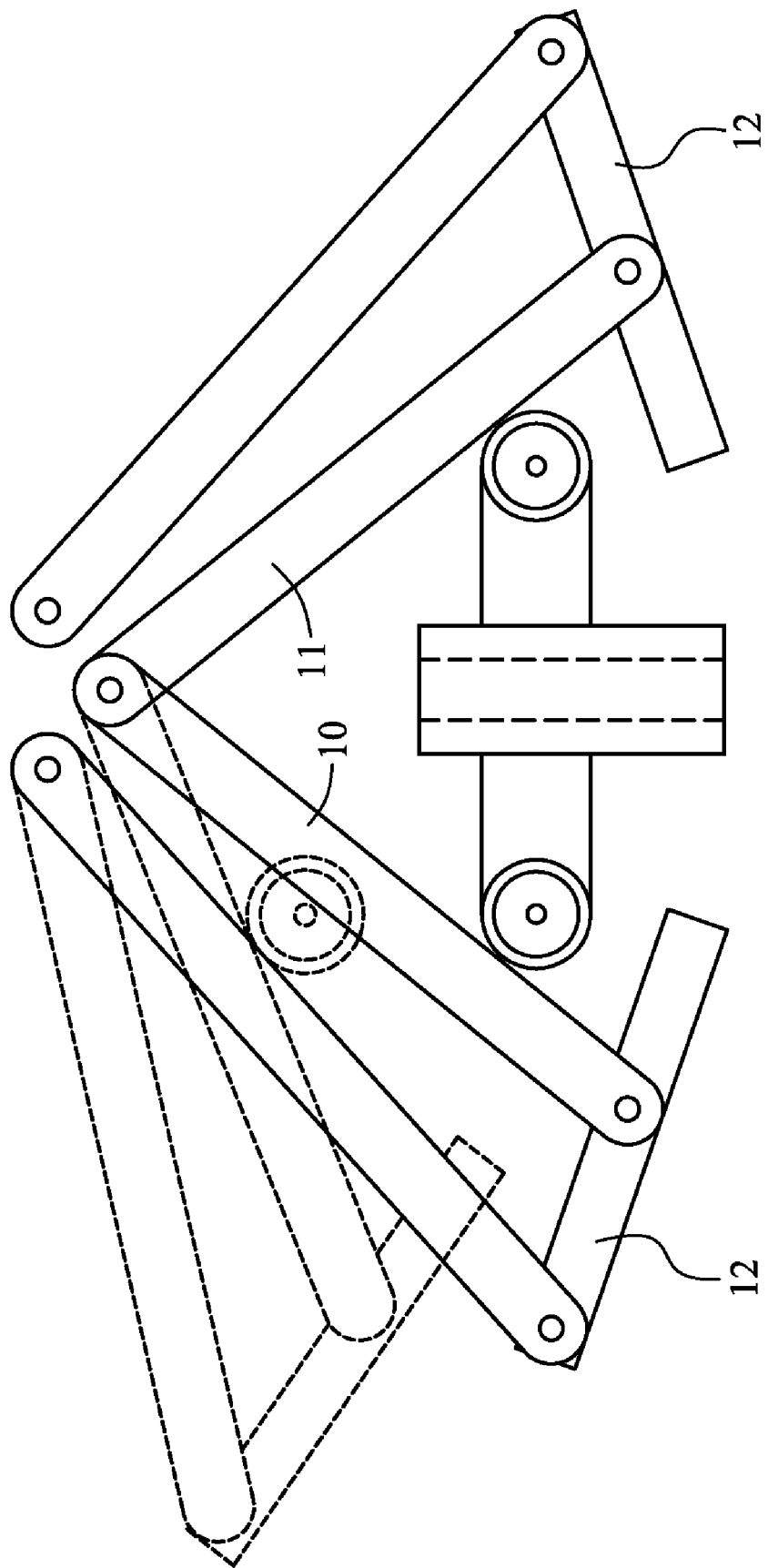
FIG. 1A and FIG. 1B are schematic diagrams using a four-bar linkage according to U.S. Pat. No. 7,265,844.
Figure 1B:
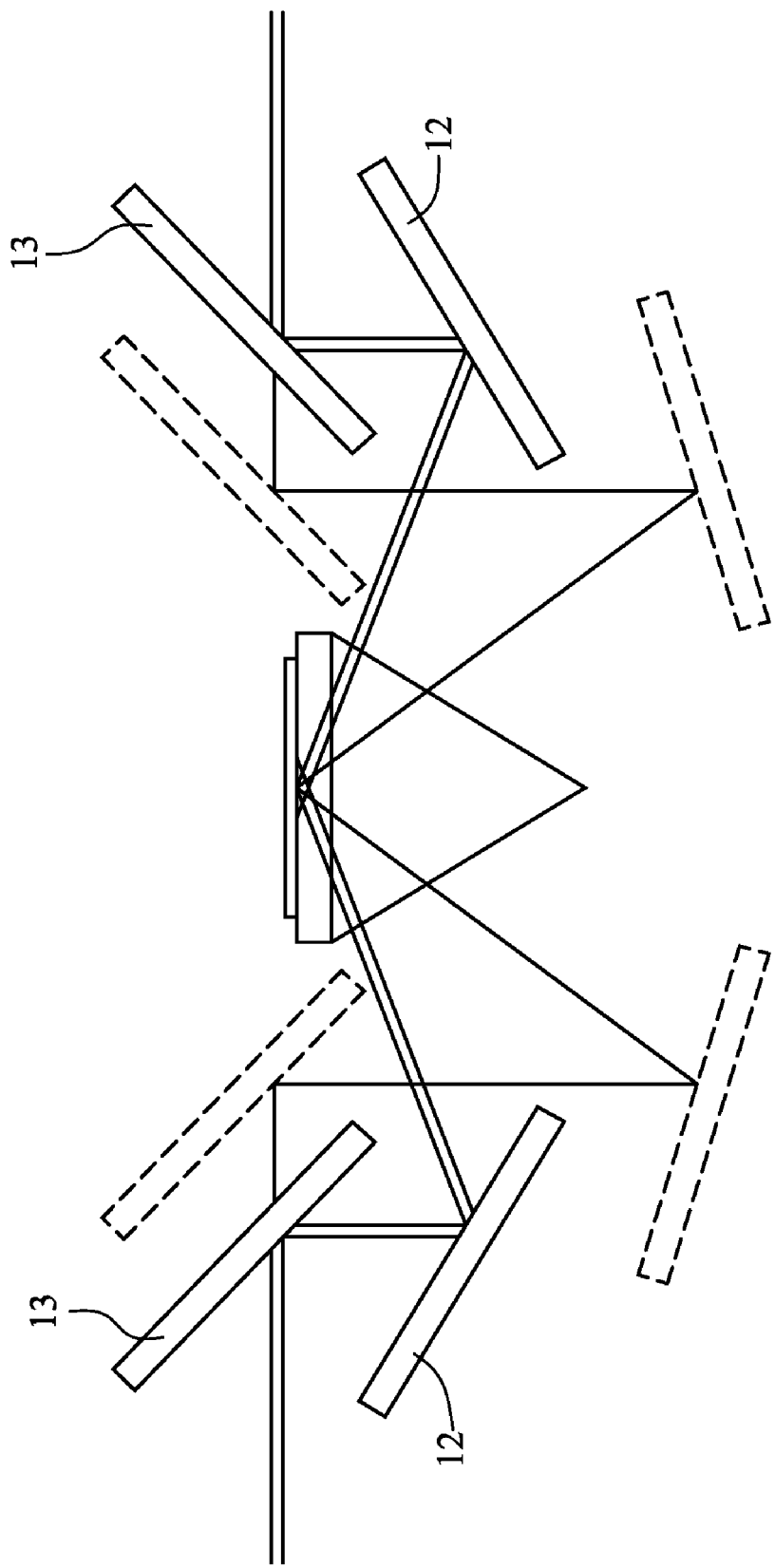
Figure 2:
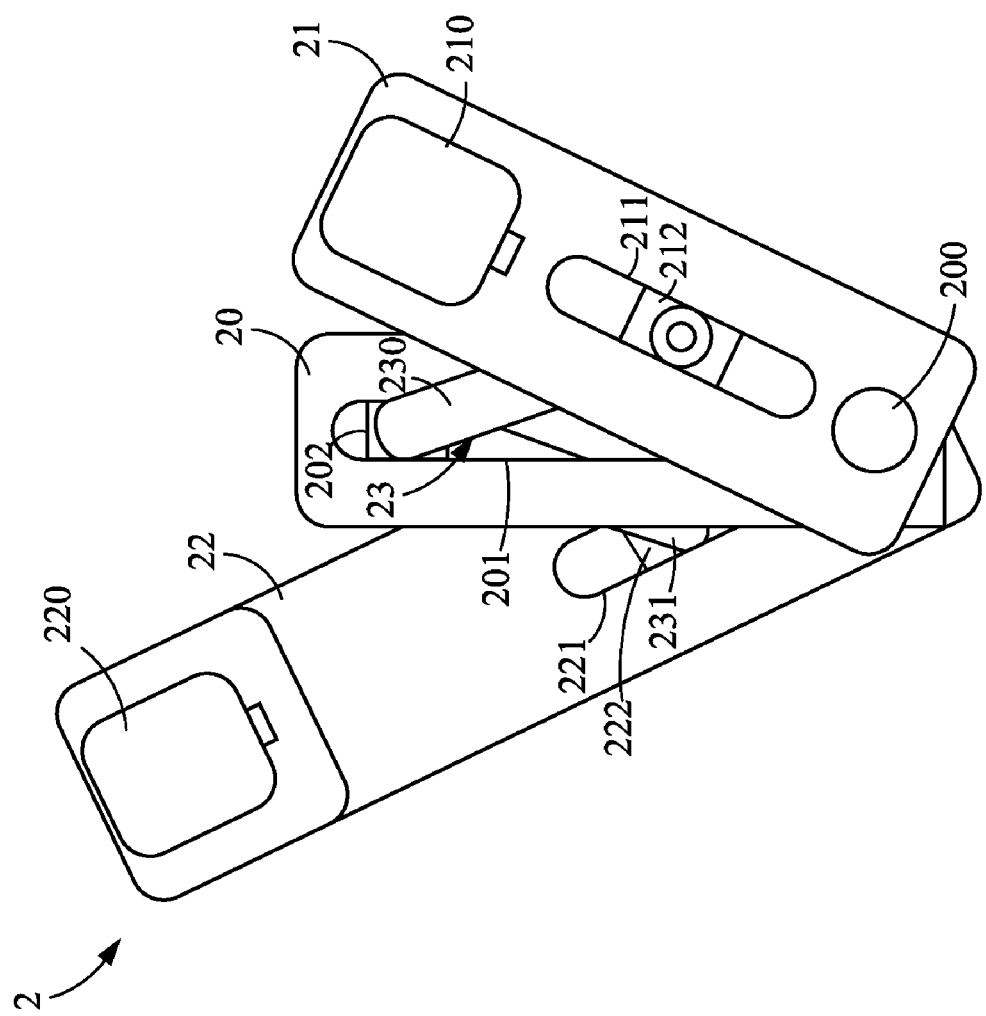
FIG. 2 is a schematic diagram of an optical inspection apparatus according to a first embodiment of the disclosure.

Please refer to FIG. 2, which is a schematic diagram of an optical inspection apparatus according to a first embodiment of the disclosure. The optical inspection apparatus comprises a feedforward control module 10, a proportional-integral-derivative (PID) control loop 20 and a compensation adder 30.

In the present embodiment, the optical inspection apparatus 2 comprises: a central shaft device 20, a first arm 21, a second arm 22 and a linkage driver portion 23. The central shaft device 20 comprises a pivot portion 200, a sliding groove 201 and a sliding object 202. The sliding object 202 is slidingly disposed in the sliding groove 201. One end of the first arm 21 is connected to the pivot portion 200. The first arm 21 is provided with a light source 210, a first sliding groove 211 and a first sliding object 212. The light source 210 is a light source capable of outputting TM polarized light source or a light source capable of outputting TM polarized light source when equipped with an additional polarizer. The first sliding object 212 is slidingly disposed in the first sliding groove 211. One end of the second arm 22 is pivotally connected to the pivot portion 200. The second arm 22 comprises a signal detector 220, a second sliding groove 221 and a second sliding object 222. The second sliding object 222 is slidingly disposed on the second sliding groove 221.

Figure 3C:
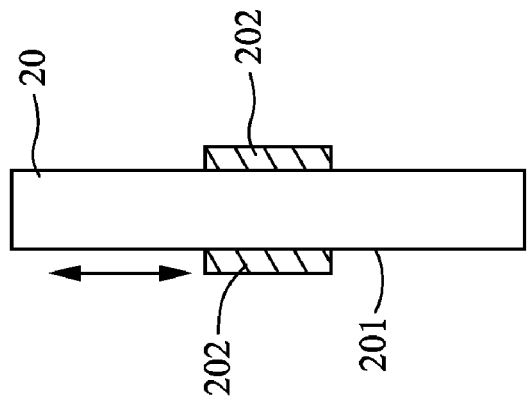
FIG. 3A to FIG. 3C are schematic diagrams showing that the sliding object is provided with a driving force according to the disclosure.
Figure 3B:
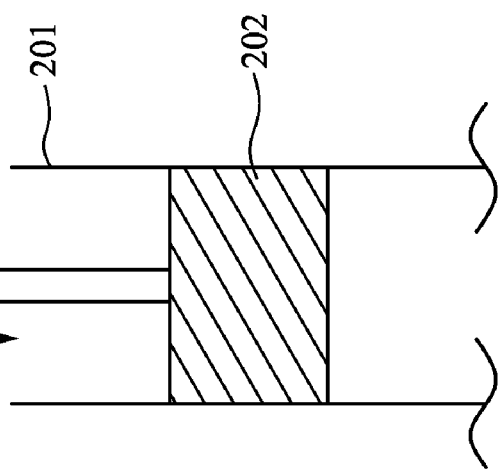
Figure 3A:
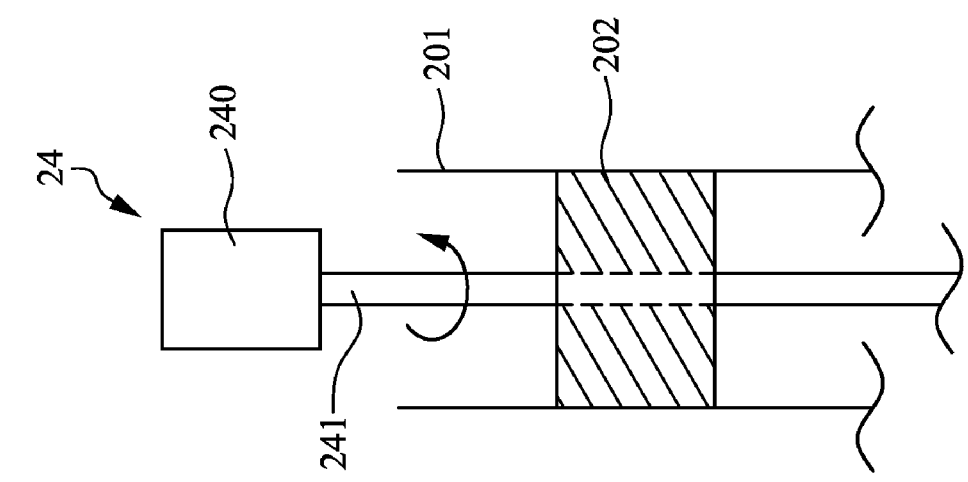

The linkage driver portion 23 is coupled to the central shaft device 20, the first arm 21 and the second arm 22. The linkage driver portion 23 is capable of driving the first arm 21 and the second arm 22 to move relatively. In the present embodiment, the linkage driver portion 23 comprises a first linkage 230 and a second linkage 231. The first linkage 230 is pivotally connected to the sliding object 202 and the first sliding object 212. The second linkage 231 is pivotally connected to the sliding object 202 and the second sliding object 222. Please refer to FIG. 3A, which is a schematic diagram showing that the sliding object is provided with a driving force according to the disclosure. In the present embodiment, a linear movement unit 24 comprising a motor 240 and a bolt 241 is coupled to the sliding object 202. The motor 240 drives the bolt 241, so that the sliding object 202 is capable of moving in the sliding groove 201. Moreover, as shown in FIG. 3B for a schematic diagram showing that the sliding object is provided with a driving force according to another embodiment, the linear movement unit 25 uses a pneumatic cylinder or hydraulic cylinder 250 capable of providing linear displacement to drive the connecting rod 251 so that the sliding object 202 moves in the sliding groove 201. Moreover, as shown in FIG. 3C, the central shaft device 20 may also be a linear motor and have a sliding object 202 thereon so that the sliding object 202 is linearly driven by the linear motor to move.

Figure 4A:
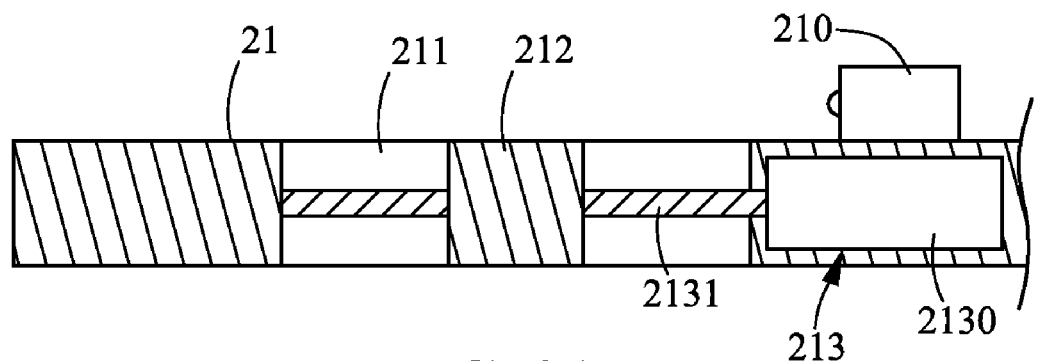
FIG. 4A to FIG. 4C are schematic diagrams showing that the first sliding object or the second sliding object is provided with a driving force according to the disclosure.
Figure 4B:
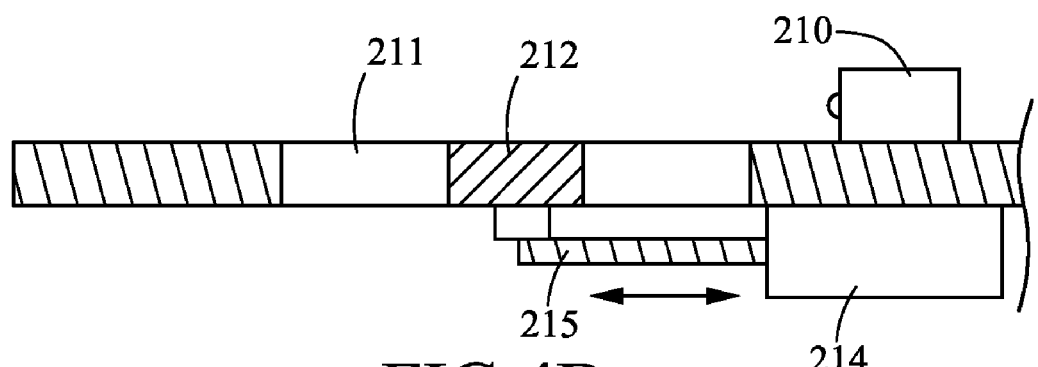
Figure 4C:
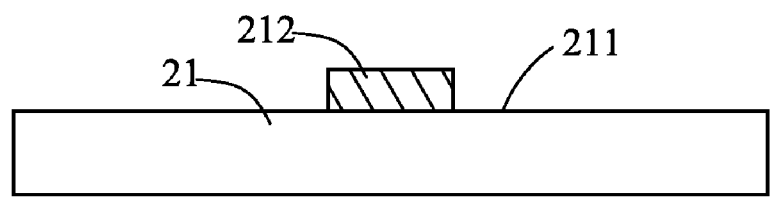

Please refer to FIG. 4A, which is a schematic diagram showing that the first sliding object or the second sliding object is provided with a driving force according to the disclosure. In FIG. 4A, the first arm 21 is provided with a first linear movement unit 213 therein. The first linear movement unit 213 uses a motor 2130 to generate a torque to drive the bolt 2131 coupled to the first sliding object 212 to rotate so that the first sliding object 212 is controlled to slide in the first sliding groove 211. The first linear movement unit 213 is not necessarily disposed in the first arm 21. Instead, the first linear movement unit 213 can also be disposed outside the first arm 21, which is readily known to anyone with ordinary skill in the art. Moreover, as shown in FIG. 4B, a pneumatic cylinder or hydraulic cylinder 214 capable of providing linear movement is used to drive the connecting rod 215 to linearly move so that the first sliding object 212 moves in the first sliding groove 211. Moreover, as shown in FIG. 4C, the first arm 21 is implemented using a linear motor. The first sliding object 212 is a sliding object on the linear motor. The configurations in FIG. 4A to FIG. 4C can all be used to drive the sliding object on the first arm or the second arm. In the present embodiment, the first arm is used to exemplify. Even though the second arm is not illustrated, the methods are the similar.

Figure 5A:
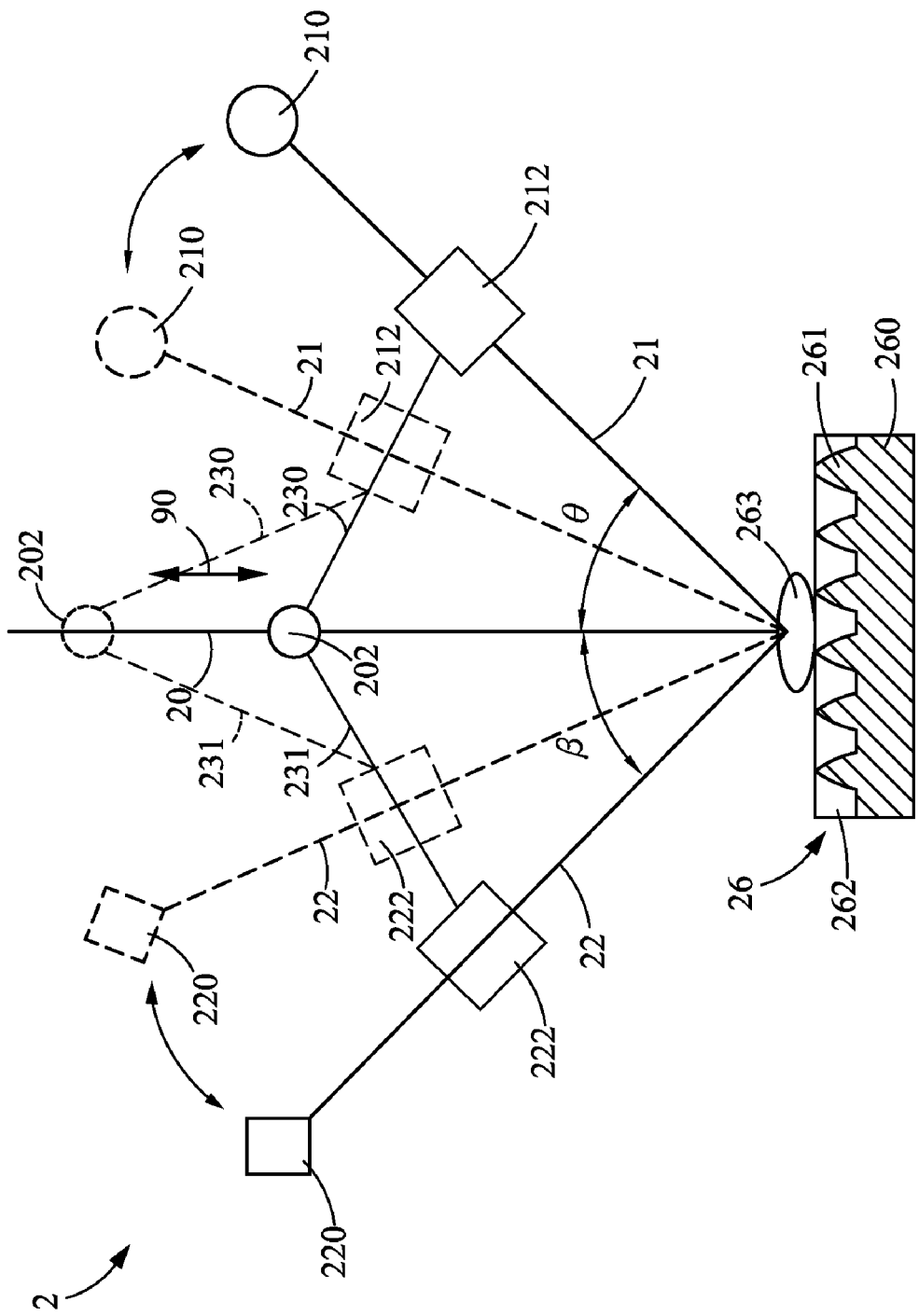
FIG. 5A and FIG. 5B are schematic diagrams showing the operations of the optical inspection apparatus in FIG. 2.
Figure 5B:
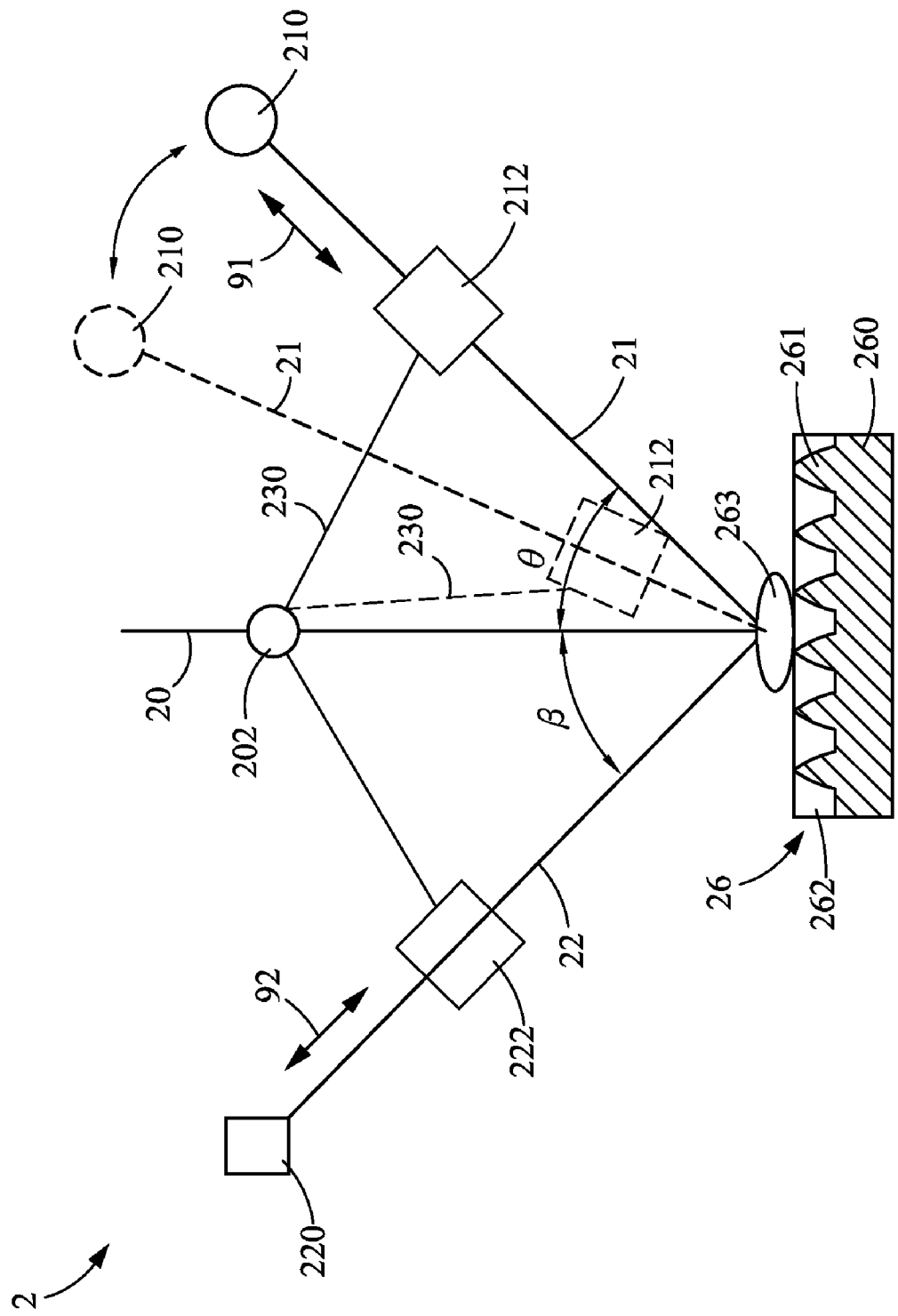

Please refer to FIG. 2, FIG. 5A and FIG. 5B, wherein FIG. 5A and FIG. 5B are schematic diagrams showing the operations of the optical inspection apparatus in FIG. 2. On one side of the optical inspection apparatus 2, a surface plasmon resonance generating and detecting portion 26 is provided. The surface plasmon resonance generating and detecting portion 26 can be a prism-type SPR detecting portion or a grating-type SPR detecting portion. In the present embodiment, the surface plasmon resonance generating and detecting portion 26 is grating-type SPR detecting portion comprising a metal layer 260 being provided with a grating 261 thereon. On the grating 261, there are biological functional groups 262 whereon an object under test 263 is dispose. In the present embodiment, the first arm 21 and the second arm 22 of the optical inspection apparatus are driven by the first linkage 230 and the second linkage 231 to relative move and change the angle θ between the first arm 21 and the central shaft device 20 and the angle β between the second arm 22 and the central shaft device 20. When the linear movement unit coupled to the sliding object 202 drives the sliding object 202 to cause a displacement 90, the first arm 21 and the second arm 22 rotate around the joint where the first sliding object 212 and the second sliding object 222 are pivotally connected if the first sliding object and the second sliding object are blocked. Therefore, the distance from the central shaft device to the first sliding object 212 and the second sliding object 222 will be changed so that the first arm 21 and the second arm 22 move outwards or inwards equally to change the angles β and θ.

Moreover, the optical inspection apparatus can also be used when the angles β and θ are not equal. In FIG. 5B, if the linear movement unit coupled to the first sliding object 212 drives the first sliding object 212 to cause a displacement 91, the first sliding object 212 on the first arm 21 moves so that the first linkage 230 rotates around the joint where the first linkage 230 is pivotally connected to the sliding object 202. In this case, the angle θ becomes larger or smaller, while the angle β remains the same. On the contrary, if the linear movement unit coupled to the second sliding object 222 drives the second sliding object 222 to cause a displacement 92, the second sliding object 222 on the second arm 22 moves so that the second linkage 231 rotates around the joint where the second linkage 231 is pivotally connected to the sliding object 202. In this case, the angle β becomes larger or smaller, while the angle θ remains the same. In the present embodiment, the linear movement unit coupled to the sliding object 202 is a long stroke linear movement unit, while the linear movement unit coupled to the first sliding object 212 and the second sliding object 222 is a high-precision linear movement unit. Therefore, when a long stroke is required, the linear movement unit coupled to the sliding object 202 is used to cause a long stroke displacement to reach a desired position. On the other hand, when high-precision tuning is required, a linear displacement unit coupled to the first sliding object 212 and the second sliding object 222 is used to drive. With the aforesaid disclosure, the emitting angle of the light source and the receiving angle of the optical inspection apparatus can be precisely controlled.

Please refer to FIG. 6A, which is a schematic diagram of an optical inspection apparatus according to a second embodiment of the disclosure. In the present embodiment, the present embodiment in FIG. 6A is similar to the embodiment in FIG. 2 except that the linkage driver portion 27 is a single rod 270. In FIG. 6A, the linkage 270 is slidingly connected to the groove of the central shaft device 20, the first arm 21 and the second arm 22. Please refer to FIG. 6B, which is a 3-D schematic diagram of the linkage in FIG. 6A. At the center, the linkage 270 comprises a sliding object 273 slidingly connected to the groove in the central shaft device 20. The linkage comprises a socket 271 and a socket 272 disposed on both sides of the linkage. Inside the socket 271 and the socket 272, sliding objects 274 and 275 are slidingly connected to the groove in the first arm 21 and the second arm 22. Moreover, the first arm 21 further comprises a stopping mechanism 28 thereon so as to stop the first arm 21 from rotating around the pivot portion 200 as an axis. Similarly, the second arm 22 also comprises a stopping mechanism so as to stop the second arm 22 from rotating around the pivot portion 200 as an axis. The structure of the stopping mechanism is conventionally well-known to anyone with ordinary skill in the art and the description thereof is thus not presented.

With the use of the linkage in FIG. 6B, the first arm 21 and the second arm 22 can relatively move outwards or inwards with equal angles or non-equal angles. For example, when the two arms 21 and 22 are unlimitedly pivotally connected to the central shaft device, the first arm 21 and the second arm 22 relatively move outwards or inwards with equal angles as the linkage 270 moves up and down. When the first arm 21 or the second arm 22 is fixed, the angles between the central shaft device 20 and the first arm 21 and the second arm 22 are not equal as the linkage 270 moves up and down. As shown in FIG. 6C, when the stopping mechanism 28 is used to fix the second arm 22, only the angle between the first arm 21 and the central shaft device 20 is changed as the linkage 270 moves up and down so that the angles between the central shaft device 20 and the first arm 21 and the second arm 22 are not equal.

Please refer to FIG. 7A and FIG. 7B, which are schematic diagrams of an optical inspection apparatus according to a third embodiment of the disclosure. In the present embodiment, the optical inspection apparatus 3 comprises a plate 30, a first arm 31, a second arm 32 and a driver portion 33. The plate 30 is provided with a guiding groove 300, a first sliding groove portion 301 and a second sliding groove portion 302 thereon. The first sliding groove portion 301 comprises a pair of first sub-sliding grooves 3010 and 3011 with the same curvature, and the second sliding groove portion 302 comprises a pair of second sub-sliding grooves 3020 and 3021 with the same curvature. Even though each of the sliding groove portions 301 and 302 in the present embodiment has a pair of sub-sliding grooves, only one sub-sliding groove or at least two sub-sliding grooves can also be used. Therefore, the numbers of sub-sliding grooves are only used to exemplify, but not to limit, the scope of the disclosure.

The first arm 31 is slidingly connected to the pair of sub-sliding grooves 3010 and 3011 and the first arm 31 further comprises a light source 310 disposed thereon. The second arm 32 is slidingly connected to the pair of second sub-sliding grooves 3020 and 3021 and the second arm 32 further comprises a detector 320 disposed thereon. The driver portion 33 is coupled to the first arm 31 and the second arm 32. The driver portion 33 applies a driving force on the first arm 31 and the second arm 32 so that the first arm 31 and the second arm 32 can move relatively on the pair of first sliding groove portions 301 and the pair of second sliding groove portions 302 to change the optical angles of the light source 310 and detector 320.

Figure 8:
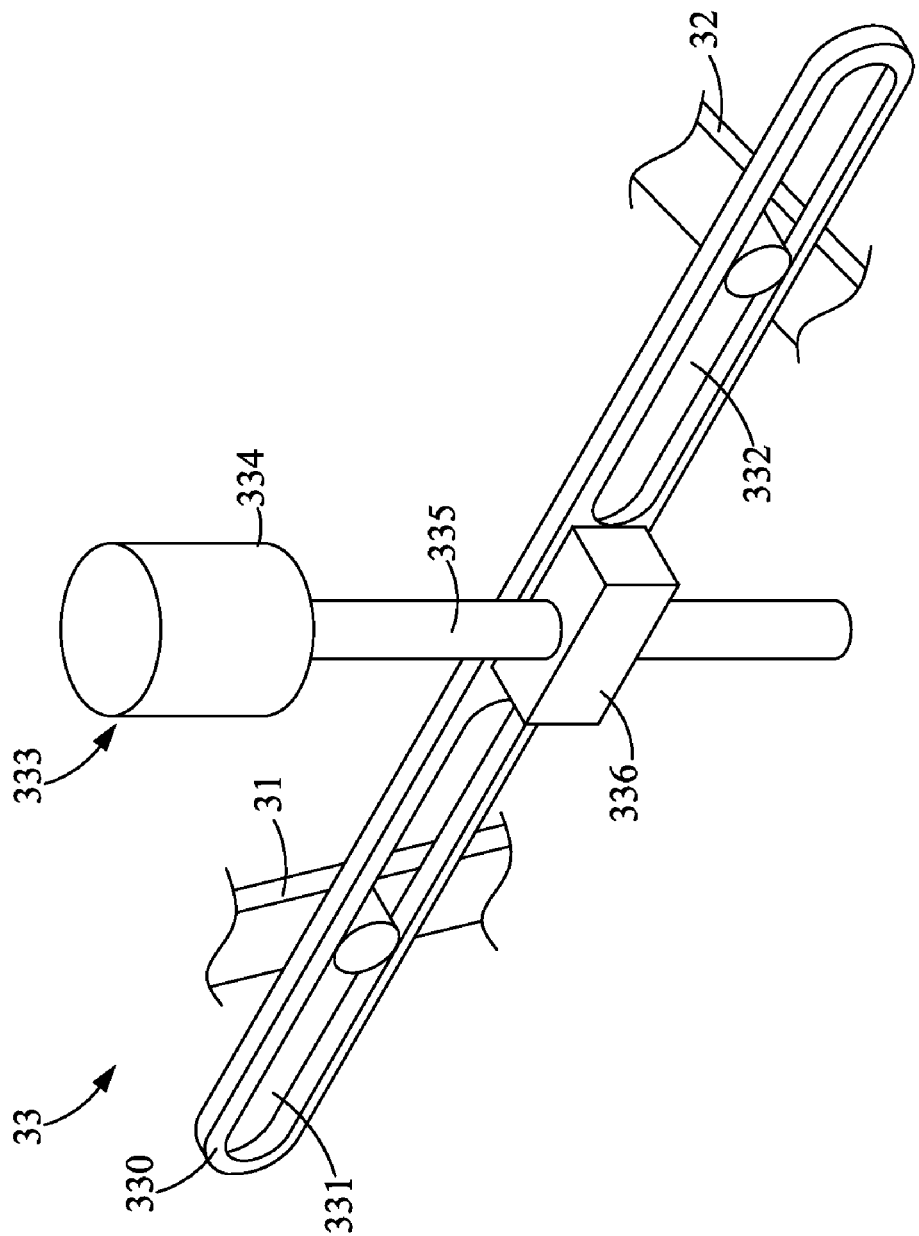
FIG. 8 is a schematic diagram of a driver portion in FIG. 7A.

As shown in FIG. 8, in the present embodiment, the driver portion 33 further comprises a linkage 330, at the center of which is slidingly connected to the guiding groove 30. The linkage 330 comprises guiding grooves 331 and 332 on both ends of the linkage 330 so as to be slidingly connected to the first arm 31 and the second arm 32, respectively. The driver portion 33 further comprises a linear movement unit 333 comprising a motor 334 and a transmission bolt 335. The motor 334 is coupled to the transmission bolt 335, and the transmission bolt 335 is screw-connected to a body 336 fixedly disposed on the linkage 330. The linear movement unit in FIG. 8 is only used to exemplify, but not to limit, the present embodiment. For example, a linear motor or a hydraulic cylinder can also be used as to provide linear displacement movement.

Returning to FIG. 7A and FIG. 7B, the operation of the optical inspection apparatus in the embodiment is described herein. The first arm 31 comprises a light source 310 disposed thereon, while the second arm 32 comprises a detector 320 disposed thereon. On one side of the optical inspection apparatus, a surface plasmon resonance generating and detecting portion 34 is provided whereon an object under test is disposed. The surface plasmon resonance generating and detecting portion 34 is a grating-type or a prism-type surface plasmon resonance generating and detecting portion. Since the surface plasmon resonance generating structure is readily known to anyone with ordinary skill in the art, description thereof is not presented herein. The light source 310 is capable of emitting a detecting light beam 3100 to the surface plasmon resonance generating and detecting portion 34. The detector 320 detects a detecting light beam 3100 generated from the surface plasmon resonance generating and detecting portion. To change the angle of light emitted from the light source 310 and the detecting for the detector 320, the linkage 330 moves linearly up and down. Since the linkage 330 is slidingly connected to the guiding groove 300, the first arm 31 and the second arm 32, the first arm 31 and the second arm 32 will be driven upwards when the linkage 330 moves upwards. Since the first arm and the second arm are slidingly connected to the first sliding groove portion 301 and the second sliding groove portion 302, the first arm and the second arm are limited to slide in the sliding groove portions 301 and 302. Therefore, the angle between the first arm 31 and the guiding groove 300 and the angle between the second arm 32 and the guiding groove 300 become smaller. Similarly, to enlarge the detecting angle and the incident angle, the linkage 330 moves downwards to drive the first arm 31 and the second arm 32 away from the guiding groove. With the use of the aforesaid mechanism, the modularization design and microminiaturization of the optical inspection apparatus can be improved and the angles can be adjusted to enlarge the detecting range and improve the inspection precision.

According to the above discussion, it is apparent that the disclosure discloses an optical inspection apparatus capable of being adapted to combine with the application of micro sensors such that practicality of modular design and miniaturization and convenience of operation can be greatly improved and that the cost can be reduced.

Although this disclosure has been disclosed and illustrated with reference to particular embodiments, the principles involved are susceptible for use in numerous other embodiments that will be apparent to persons skilled in the art. This disclosure is, therefore, to be limited only as indicated by the scope of the appended claims.

What is claimed is:

1. An optical inspection apparatus, comprising:
    a central shaft device comprising a pivot portion;
    a first arm with one end pivotally connected to said pivot portion, said first arm being provided with a light source thereon;
    a second arm with one end pivotally connected to said pivot portion, said second arm being provided with a detector thereon; and
    a linkage driver portion coupled to said central shaft device, said first arm and said second arm, said linkage driver portion being capable of conducting a movement to drive said first arm and said second arm to move relatively, wherein said linkage driver portion further comprises:
        a first linkage coupled to said central shaft device and said first arm, said first linkage being used to drive said first arm and said central shaft device to move relatively through force; and
        a second linkage coupled to said central shaft device and said second arm, said second linkage used to drive said second arm and said central shaft device to move relatively through a driving force;

wherein said central shaft device further comprises a sliding groove with a sliding object disposed thereon, said sliding groove being pivotally connected to said first linkage and said second linkage; said first arm further comprises a first sliding groove with a first sliding object disposed thereon, said first sliding groove being pivotally connected to said first linkage, and said second arm further comprises a second sliding groove with a second sliding object disposed thereon, said second sliding groove being pivotally connected to said second linkage, said sliding object being coupled to a linear movement unit being capable of providing said sliding object with said driving force applied thereon, said first sliding object being coupled to a first linear movement unit being capable of providing said first sliding object with said driving force applied thereon, said second sliding object being coupled to a second linear movement unit being capable of providing said second sliding object with said driving force applied thereon.

2. The optical inspection apparatus as recited in claim 1, further comprising a surface plasmon resonance generating and detecting portion to generate surface plasmon resonance.

3. The optical inspection apparatus as recited in claim 2, wherein said surface plasmon resonance generating and detecting portion is a prism-type surface plasmon resonance detecting portion.

4. The optical inspection apparatus as recited in claim 2, wherein said surface plasmon resonance generating and detecting portion is a grating-type surface plasmon resonance detecting portion.

5. The optical inspection apparatus as recited in claim 1, wherein said first arm further comprises a stopping mechanism disposed thereon.

6. The optical inspection apparatus as recited in claim 1, wherein said second arm further comprises a stopping mechanism disposed thereon.

7. An optical inspection apparatus, comprising:
a first arm being slidingly connected to a first sliding groove portion with a curvature, said first arm further comprising a light source disposed thereon;
a second arm being slidingly connected to a second sliding groove portion with a curvature, said second arm further comprising a detector disposed thereon; and
a driver portion being coupled to said first arm and said second arm and used to apply a driving force on said first arm and said second arm to drive said first arm and said second arm to move respectively on said first sliding groove portion and said second sliding groove portion, wherein said driver portion further comprises:
a linear movement unit capable of providing a driving force;
a second arm being slidingly connected to a second sliding groove portion with a curvature, said second arm further comprising a detector disposed thereon; and
a linkage being slidingly disposed on a plate and being coupled to said linear movement unit, said linkage further comprising on both sides thereof a socket, each being slidingly connected to said corresponding first arm and said corresponding second arm, said linkage using said driving force to perform a linear displacement movement.

8. The optical inspection apparatus as recited in claim 7, wherein said first sliding groove portion comprises a first sub-sliding groove or a plurality of first sub-sliding grooves, while said second sliding groove portion comprises a second sub-sliding groove or a plurality of pairs of second sub-sliding grooves.

9. The optical inspection apparatus as recited in claim 7, further comprising a surface plasmon resonance generating and detecting portion to generate surface plasmon resonance.

10. The optical inspection apparatus as recited in claim 9, wherein said surface plasmon resonance generating and detecting portion is a prism-type surface plasmon resonance detecting portion.

11. The optical inspection apparatus as recited in claim 9, wherein said surface plasmon resonance generating and detecting portion is a grating-type surface plasmon resonance detecting portion.

12. An optical inspection apparatus, comprising:
a central shaft device comprising a pivot portion;
a first arm with one end pivotally connected to said pivot portion, said first arm being provided with a light source thereon;
a second arm with one end pivotally connected to said pivot portion, said second arm being provided with a detector thereon; and
a linkage slidingly connected to said first arm, said second arm and said central shaft device and coupled to a linear movement unit, said linkage being capable of conducting a movement to drive said first arm and said second arm to move relatively, wherein said linkage comprises a sliding object slidingly connected to a groove in the central shaft device, and a first socket and a second socket respectively disposed on both sides of the linkage, wherein the first socket comprises a first sliding object slidingly connected to a first groove in the first arm and the second socket comprises a second sliding object slidingly connected to a second groove in the second arm.

* * * * *